(12) United States Patent
Markusson et al.

(10) Patent No.: US 12,016,878 B2
(45) Date of Patent: Jun. 25, 2024

(54) COMPOSITION FOR TREATING AND/OR PREVENTING VESTIBULODYNIA

(71) Applicant: PEPTONIC MEDICAL AB, Bromma (SE)

(72) Inventors: Dan Markusson, Växjö (SE); Johan Inborr, Stockholm (SE); Erik Sundquist, Saltsjöbaden (SE)

(73) Assignee: PEPTONIC MEDICAL AB, Bromma (SE)

( * ) Notice: Subject to any disclaimer, the term of this patent is extended or adjusted under 35 U.S.C. 154(b) by 0 days.

(21) Appl. No.: 17/921,426

(22) PCT Filed: Apr. 26, 2021

(86) PCT No.: PCT/EP2021/060831
§ 371 (c)(1),
(2) Date: Oct. 26, 2022

(87) PCT Pub. No.: WO2021/219545
PCT Pub. Date: Nov. 4, 2021

(65) Prior Publication Data
US 2024/0041916 A1 Feb. 8, 2024

(30) Foreign Application Priority Data
Apr. 28, 2020 (SE) .................... 2050480-9

(51) Int. Cl.
| A61K 31/717 | (2006.01) |
| A61K 9/00 | (2006.01) |
| A61K 47/12 | (2006.01) |
| A61P 15/02 | (2006.01) |

(52) U.S. Cl.
CPC .......... *A61K 31/717* (2013.01); *A61K 9/0034* (2013.01); *A61K 47/12* (2013.01); *A61P 15/02* (2018.01)

(58) Field of Classification Search
CPC ...... A61K 31/717; A61K 9/0034; A61P 15/02
See application file for complete search history.

(56) References Cited

U.S. PATENT DOCUMENTS

| 2015/0272986 A1 | 10/2015 | Einar |
| 2017/0239181 A1 | 8/2017 | Oshry et al. |

FOREIGN PATENT DOCUMENTS

| CA | 3064658 A1 | 12/2018 |
| EP | 3603627 A2 | 2/2020 |
| WO | WO 2014/057096 | 4/2014 |
| WO | WO 2018/219747 | 12/2018 |
| WO | WO-2018219747 A1 * | 12/2018 | ........... A61K 31/717 |

OTHER PUBLICATIONS

Nunns, "Vulvodynia management", Mar. 2015, Obstetrics, Gynaecology and Reproductive Medicine, vol. 25, Issue 3, pp. 68-74. (Year: 2015).*
Malopesza-Jarmolowska, K., "The properties of Intravaginal Globules Containing a Lactic Acid-Chitosan Complex", Prog. Chem. Appl. Chitin. Deriv., vol. 24, 2019, pp. 127-134.
International Search Report and Written Opinion dated Jul. 26, 2021 by the International Searching Authority for International Application No. PCT/EP2021/060831 filed on Apr. 26, 2021 and published as WO 2021/219545 (Applicant—Potter Clarkson) (9 pages).
International Preliminary Report on Patentability was completed on Aug. 2, 2022 by the European Patent Office for International Application No. PCT/EP2021/060831 filed on Apr. 26, 2021 and published as WO 2021/219545 (Applicant—Potter Clarkson) (19 pages).

* cited by examiner

*Primary Examiner* — Michael B. Pallay
(74) *Attorney, Agent, or Firm* — Ballard Spahr LLP

(57) ABSTRACT

Described is a method for treating and/or preventing vestibulodynia by administering a therapeutically effective amount of a composition to a subject in need thereof The composition can include at least one non-ionic cellulose ether being hydroxypropylmethylcellulose (HPMC), one or more pH regulating agent(s) that includes a lactate and/or a citrate buffer , and water. The composition can have a pH from 3 to 5, a viscosity from 35000 to 100 000 mPas, said viscosity being measured at 20° C. according to European Pharmacopeia 7.0, 2.210, and being free from any additional active pharmaceutical agent, wherein the composition includes from 1 wt % to 5 wt % of said non-ionic cellulose ether based on the total weight of the composition.

20 Claims, 4 Drawing Sheets

COMPOSITION FOR TREATING AND/OR PREVENTING VESTIBULODYNIA

CROSS-REFERENCE TO RELATED APPLICATIONS

This application is a U.S. National Phase Application of International Application No. PCT/EP2021/060831, filed Apr. 26, 2021, which claims priority to Swedish Application No. 2050480-9, filed Apr. 28, 2020, each of which are hereby incorporated by reference in their entirety.

TECHNICAL FIELD

The present document is directed to a composition for use in the treatment and/or prevention of vestibulodynia. The composition may be a gel comprising a non-ionic cellulose ether and the treatment involves administration of the gel to the vulva and/or the vaginal introitus.

BACKGROUND

Vulvar vestibulitis syndrome (VVS), vestibulodynia, or vulvar vestibulitis, is vulvodynia localized to part or the whole of the vulvar vestibule. Vestibulodynia is a chronic pain disorder which lasts for three months or more. The symptoms of vestibulodynia include a localized burning, aching, itching or cutting kind of pain in the vestibular area, often in connection with touching or applying a pressure on this area. The pain may be provoked by e.g. the insertion of a tampon or a penis or with the pressure from sitting, or it may be constant. The pain may occur at the first penetration (primary vulvar vestibulitis) or after a period of time with pain-free penetration (secondary vulvar vestibulitis). Further, the vestibulodynia may be unprovoked, i.e. the pain occurs without any trigger and is present regardless whether the area is touched or not.

Little is known about the cause of vestibulodynia. It has been speculated that sub-clinical human papillomavirus infection, chronic recurrent candidiasis, or chronic recurrent bacterial vaginosis may be involved. Also, muscular causes have been suggested, as a result of chronic hypertonic perivaginal muscles, leading to vaginal tightening and pain. In addition, neurological causes have been implied. Psychological factors may contribute to or increase the problem, leading to a lowered sex drive and difficulties in becoming aroused.

Vestibulodynia is sometimes confused with dyspareunia. However, dyspareunia concerns pelvic or vaginal pain associated with sexual intercourse. In other words, the pain symptoms of dyspareunia always occur with provoking. In contrast, vestibulodynia is localized to the vulva and vaginal introitus only. Thus, vestibulodynia does not occur in the vagina or pelvic. Further, vestibulodynia is chronic.

WO 2018/219747 discloses a pharmaceutical composition comprising at least one non-ionic cellulose ether, wherein said composition has a viscosity of 35000 cP or more, an osmolality of from about 10 to about 300 mOsmol/kg, and a pH of from about 3 to about 4. The composition may be used in the treatment and/or prevention of a climacteric disorder, wherein said climacteric disorder is a selected from the group consisting of vaginal dryness, vaginal irritation, vaginal itching, dysuria, dyspareunia, and/or vaginal bleeding during and/or after sexual intercourse and any combination thereof.

WO 2014/057096 discloses a composition for alleviating conditions associated with vaginal dryness. The composition comprises a thickener, a non-ionic water-soluble poly(ethylene oxide)polymer having a molecular weight of at least 100,000 Da, and at least 95 wt % water. It is described that the composition alleviates conditions associated with vaginism or vestibulitis.

There is currently no cure for vestibulodynia, but there are a number of ways to lessen the symptoms. Medications to lessen the symptoms of vestibulodynia typically include local anaesthetics, estrogen treatment, nerve blocks, anti-inflammatory medications (e.g. steroids) and botox, i.e. botulinum toxin. Also, muscular exercise of the vaginal and pelvic muscles, transcutaneous electrical nerve stimulation, and even surgery to remove painful tissue have been used as therapies for vestibulodynia. There is no single treatment that helps all women suffering from vestibulodynia, and finding an appropriate treatment often involves a lengthy trial and error process.

It is an object of the present disclosure to alleviate at least one of the problems discussed above, and/or to provide advantages and aspects not provided by hitherto known technique.

SUMMARY

The present document is directed to composition comprising at least one non-ionic cellulose ether for use in the treatment and/or prevention of vestibulodynia, wherein said composition does not comprise an active pharmaceutical agent. The viscosity of the composition may be at least about 35000, at least about 38 000, at least about 40 000, at least about 45 000, at least about 47 000, at least about 50 000, at least about 52 000 or at least about 55 000 mPas. For example, the viscosity may be from about 35 000 to about 100 000, from about 38 000 to about 100 000, from about 40 000 to about 100 000, from about 45 000 to about 100 000, from about 47 000 to about 100 000, from about 50 000 to about 100 000, from about 52 000 to about 100 000 or from about 55 000 to about 100 000 mPas. The viscosity may after storage at room temperature for about six months be at least about 38 000, at least about 40 000, at least about 42 000, at least about 45 000, at least about 50 000, at least about 52 000 or at least about 55 000 mPas.

The osmolality of the composition may be from about 10 to about 300 mOsmol/kg, from about 10 to about 250 mOsmol/kg, from about 10 to about 200 mOsmol/kg, such as from about 20 to about 100 mOsmol/kg, from about 30 to about 50 mOsmol/kg, or from about 40 to about 50 mOsmol/kg.

The pH of the composition may be within the range of from about 3 to about 5, from about 3 to about 4.5, such as from about 3.2 to about 4.0, from about 3.5 to about 4.0, or from about 3.7 to about 3.9, such as 3.8. The pH may be regulated by the presence of a pH regulating agent in said composition, such as a buffer, such as a lactate and/or citrate buffer.

The composition may further comprise a preservative, such as benzoic acid.

The at least one non-ionic cellulose ether may be selected from the group consisting of methylcellulose (MC), hydroxypropylcellulose (HPC), hydroxypropylmethylcellulose (HPMC), hydroxyethylethylcellulose (HEEC), hydroxyethylmethylcellulose (HEMC) and any combination thereof. A preferred non-ionic cellulose ether is hydroxypropylmethylcellulose (HPMC). The amount of non-ionic cellulose ether in the composition may be from about 1 wt % to about 5 wt %, such as from about 2 wt % to about 4 wt %, such as from about 3 wt % to about 4 wt %, such as about 3 wt % to about 3.5 wt %, such as 3.2 wt %.

An exemplary composition may comprise or consist of from about 3 wt % to about 4 wt %, such as about 3 wt % to about 3.5 wt %, such as 3.2 wt % hydroxypropylmethylcellulose (HPMC), a lactate buffer in a concentration of from about 20 mM to about 40 mM and optionally a preservative, such as benzoic acid, in at a concentration of from about 0.5 mg/g to about 1.5 mg/g, said composition having a pH within the range of from about 3.5 to about 4, such as about 3.8.

The composition may be administered at least once daily, such as one to five times a day.

The composition may be administered to the vulva and/or the vaginal introitus. For administration to the vulva, an amount of from about 0.5 to 1.5 ml is usually suitable. For administration to the vaginal introitus, an amount of from about 0.5 to about 1.5 ml to the vagina is usually suitable.

The present document is also directed to a method for treating and/or preventing vestibulodynia, said method comprising administering a therapeutically effective amount of a composition as defined herein to a subject in need thereof.

The present document is also directed to the use of a non-ionic cellulose ether for the manufacture of a composition as defined above for the treatment and/or prevention of vestibulodynia Other features and advantages of the invention will be apparent from the following detailed description, drawings, examples, and from the claims.

DEFINITIONS

Figure 1:
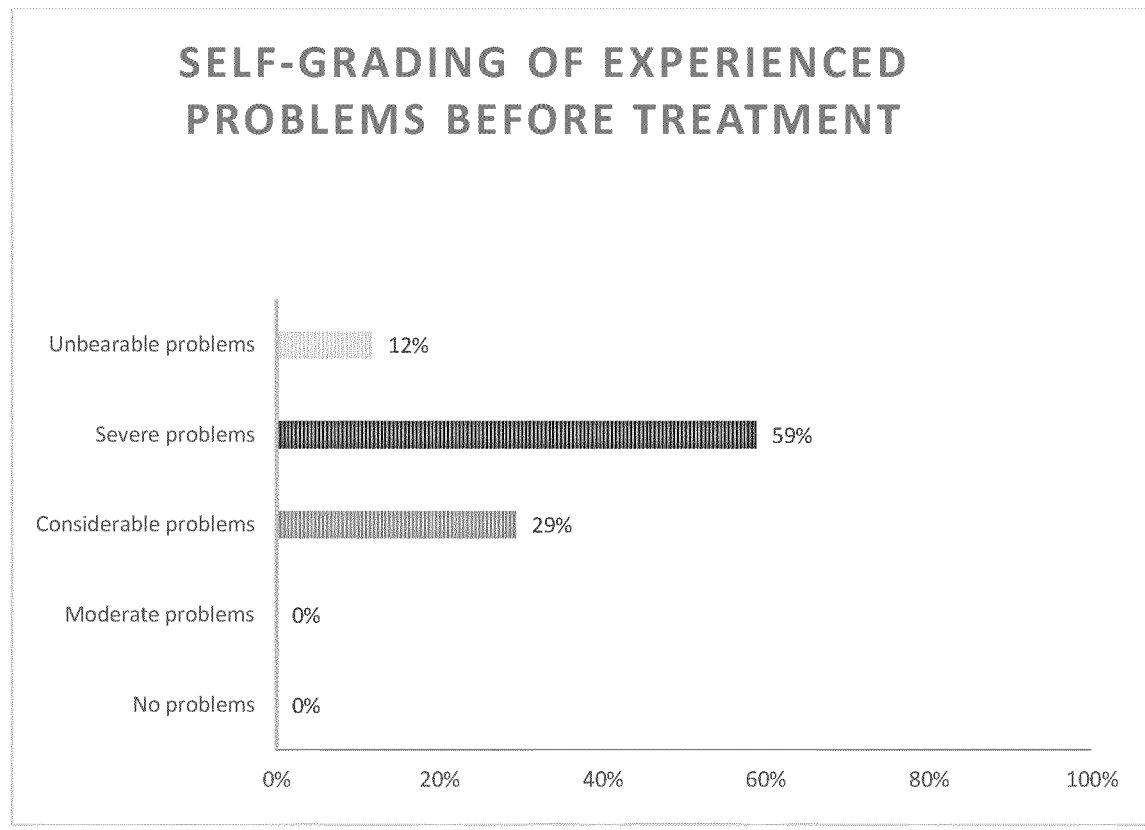
FIG. 1 show a grading of the experienced problems with vestibulodynia before treatment with the composition of Example 2.

In the context of the present document the terms vulvar vestibulitis syndrome (VVS), vestibulodynia, and vulvar vestibulitis may be used interchangeably and relates to vulvodynia localized to the vulvar vestibule. Vestibulodynia is a chronic pain syndrome that affects the vulvar area, and which does not appear to have any identifiable cause.

A "pH regulating agent" is any agent, such as a liquid agent, such as an aqueous liquid agent, which is able to regulate and/or maintain the pH of said pharmaceutical composition, wherein said pH is kept approximately in a selected range, which selected range is exemplified herein. Such a pH regulating agent can for example be a buffer, such as a citrate, lactate or phosphate buffer. A "buffer" is an ionic compound, usually a salt of a weak acid or base, added to a solution to resist changes in its acidity or alkalinity and thus stabilizes its pH. A buffer solution is a solution containing such a compound. Other examples of a pH regulating agents are organic and inorganic acids and bases, such as acetic acid, citric acid, phosphoric acid, hydrochloric acid and sodium hydroxide.

The cellulose ethers used in the composition disclosed in this document are non-ionic, with alkyl and/or hydroxyalkyl groups attached to the anhydroglucose units by ether linkages, which form hydroxyalkylalkylcelluloses, wherein the alkyl groups have from 1 to 4 carbon atoms.

Representative cellulose ethers for use in the pharmaceutical compositions according to the present invention are methylcellulose (MC), hydroxyethylmethylcellulose (HEMC), hydroxypropylmethylcellulose (HPMC), hydroxyethylethylcellulose (HEEC), and hydroxypropylcellulose (HPC). These polymers have substituents that are either nonpolar (e.g. methyl) or slightly polar (e.g. hydroxyethyl), which in combination with the hydrophilic cellulose backbone provide an amphiphilic polymer.

The viscosity of the pharmaceutical composition disclosed herein was measured at 20° C. according to European Pharmacopoeia 7.0, 2.2.10, e.g. using spindle viscometer Brookfield DV-I Prime with spindle number SC4-28 at 1 rpm (revolutions per minute) unless otherwise specified. The torque value should be ≥10% for the result to be stable and reliable. The Brookfield instrument will display a warning light if the torque value is <10%. The correct performance of the instrument was regularly checked with reference standards (oils with different viscosities) supplied by Brookfield. The viscosity is given in mPas (centipoise, wherein 1 mPas is 1 mPa·s).

By "composition" is in the context of the present document intended a composition suitable for medical use. The composition may thus also be denoted a "medical composition" or a "pharmaceutical composition".

"Osmolality" is an expression of solute osmotic concentration per mass of solvent measured in mOsmolal or mOsmol per kg solvent, i.e. mOsmol/kg.

By room temperature is meant a temperature of about 20-25° C., i.e. within the range of from about 20° C. to about 25° C. such as about 22° C.

As used herein, wt % stands for weight percent, i.e. percent by weight.

As used herein, rpm stands for revolutions per minute.

DESCRIPTION

The present document is based on the surprising finding that a composition comprising at least one non-ionic cellulose ether wherein said composition does not comprise an active pharmaceutical agent, can be successfully used in the treatment and/or prevention of vestibulodynia (also denoted vulvar vestibulitis syndrome or vulvar vestibulitis).

As used herein, vestibulodynia is understood to comprise or consist of pain affecting the vulvar region and optionally also the vaginal introitus, i.e. entrance to the vagina. The vestibulodynia may be generalized vestibulodynia, i.e. vestibulodynia affecting the entire vulvar region and optionally also the introitus to the vagina. Additionally or alternatively, the vestibulodynia may be localized vestibulodynia, i.e. vestibulonia affecting the vulval vestibule and optionally also the vaginal introitus.

Vestibulodynia is a chronic disorder, i.e. a disorder taking place during three months or more. The vestibulodynia may be unprovoked, i.e. the vestibulodynia occurs without any trigger and is present regardless whether the area is touched or not. Thus, the vestibulodynia may occur in the absence of touching or application of pressure to the vulva and/or vaginal introitus. Additionally or alternatively, the vestibulodynia may be provoked, i.e. the vestibulodynia occurs in the presence of touching or application of pressure to the vulva and/or vaginal introitus. Further, vestibulodynia may or may not be associated with sexual intercourse.

The Composition

The composition to be used according to the present document in the treatment and/or prevention of vestibulodynia is based on one or more non-ionic cellulose ethers. The non-ionic cellulose ether is selected from the group consisting of methylcellulose (MC), hydroxypropylcellulose (HPC), hydroxypropylmethylcellulose (HPMC), hydroxyethylethylcellulose (HEEC), hydroxyethylmethylcellulose (HEMC) and any combination of two or more thereof. A preferred non-ionic cellulose ether is hydroxypropylmethylcellulose (HPMC).

Cellulose ethers are named after, and based on, cellulose which is a renewable material and the most common organic chemical compound in nature. There is a broad range of cellulose ethers available on the market, both ionic and non-ionic, for example sodium carboxymethylcellulose, hydroxyethylethylcellulose, hydroxyethylcellulose, hydroxypropylcellulose, hydroxyethylmethylcellulose and hydroxypropylmethycellulose.

Cellulose ethers are used as additives in such diverse applications as food, paint, oil recovery, paper, cosmetics, pharmaceuticals, adhesives, printing, agriculture, ceramics, textiles, detergents and building materials. Cellulose ethers improve the product quality in these applications and act as thickeners, water retention agents, suspending aids, protecting colloids, film formers or thermoplastics in such different products as dispersion paints, drilling muds, ice cream, tablet coatings, wallpaper paste and tile adhesive.

Non-ionic cellulose ethers such as methylcellulose, hydroxypropylmethylcellulose (also referred to as hypromellose) and methylhydroxyethylcellulose, are widely used in the pharmaceutical industry due to their ability to thicken, bind and retain water, as well as to emulsify and suspend particles and form films. Further information regarding non-ionic cellulose ethers can be found e.g. in WO92/09307.

The composition comprises from about 1 wt % to about 5 wt % of non-ionic cellulose ether(s), based on the total weight of the composition, such as from about 2 wt % to about 4 wt %, such as from about 3 wt % to about 4 wt %, such as about 3 wt % to about 3.5 wt %, such as about 1.5 wt %, 2 wt %, 2.5 wt %, 3 wt %, 3.2 wt %, 3.5 wt %, 4 wt %, or 4.5 wt % non-ionic cellulose ether. For instance, the composition may comprise from about 2.5 wt % to about 3.5% wt % non-ionic cellulose ether. If more than one non-ionic cellulose ether is present, the respective different non-ionic cellulose ethers may be present in different amounts. However, as mentioned herein, due to the variation in chain lengths between different batches of non-ionic cellulose ethers, the actual amount of non-ionic cellulose ether must be adjusted to achieve the desired viscosity.

The viscosity as defined in this document is determined as described above by measurement at 20° C. according to Ph. Eur. 2.2.10. The viscosity values referred to herein were measured at 1 rpm unless otherwise specified.

The composition to be used according to the present document for the treatment and/or prevention of vestibulodynia may have a viscosity of at least about 35 000, at least about 38 000, at least about 40 000, at least about 45 000, at least about 47 000, at least about 50 000, at least about 52 000 or at least about 55 000 mPas. For example, the viscosity may be from about 35 000 to about 100 000, from about 38 000 to about 100 000, from about 40 000 to about 100 000, from about 45 000 to about 100 000, from about 47 000 to about 100 000, from about 50 000 to about 100 000, from about 52 000 to about 100 000 or from about 55 000 to about 100 000 mPas. The composition may have the aforementioned viscosity when freshly prepared. Additionally, the composition may also have such a viscosity after storage at room temperature for about six months. The storage stability of the composition as regards viscosity may be affected by the storage conditions. For example, storing the composition refrigerated and/or in glass containers may reduce the viscosity reduction during storage. The viscosity of the composition is important in order to ensure that the composition can be easily applied to the area of application, i.e. that it is not too "runny".

When a certain viscosity of the composition is desired, the amount of non-ionic cellulose ether used in the pharmaceutical composition is selected so that the desired viscosity is obtained. As is known to the person skilled in the art of pharmaceutical development, the chain length of the non-ionic cellulose ethers is one parameter that affects the viscosity obtained, with shorter chain lengths providing a lower final viscosity when a certain concentration of non-ionic cellulose ethers is used than if the same concentration of non-ionic cellulose ethers with a longer chain length is used. As is also known to the person skilled in the art of pharmaceutical development, there is always a variation in the chain lengths in every batch of non-ionic cellulose ethers, which variation can be small or large. However, it is the mean chain length that affects the viscosity.

As mentioned above, the viscosity of the composition may thus be regulated e.g. by the amount of non-ionic cellulose ether used and/or the type of non-ionic cellulose ether. Non-ionic cellulose ethers are polymers, the chain length of which may vary. A longer chain length results in a higher viscosity for a given wt % of non-ionic cellulose ether in the composition.

The composition may have an osmolality from about 10 to about 300 mOsmol/kg, such as from about 10 to about 200 mOsmol/kg, from about 20 to about 100 mOsmol/kg, from about 30 to about 50 mOsmol/kg, or from about 40 to about 50 mOsmol/kg.

The pH of the composition may be from about 3 to about 5, such as from about 3 to about 4.5, such as about 3.2 to about 4.0, from about 3.5 to about 4.0, or from about 3.7 to about 3.9, such as about 3.8. The pH may be regulated by the presence of a pH regulating agent in said composition, such as a buffer. Typically, a lactate or a citrate buffer is used, or a combination thereof. Alternatively, or additionally, an acid or base, such as hydrochloric acid or sodium hydroxide may be used to regulate the pH.

The concentration of a pH-regulating agent in the composition may be from about 20 to about 100 mM, such as from about 20 mM to about 100 mM, or from about 20 to about 75 mM, from about 20 mM to about 50 mM, from about 20 to about 40 mM, or from about 20 to about 30 mM, such as 25 mM, in an aqueous solution. It should be noted that these values are not exact, meaning that they can vary slightly around the values provided. Depending on which pH is required and which buffer is used in the composition, the concentration of the pH regulating agent will vary accordingly.

The composition may further comprise a preservative, such as benzoic acid. When benzoic acid is used as a preservative, it may be added in an amount of approximately 0.5-1.5 mg/g composition, such as about 0.6, 0.7, 0.8, 0.9, 1.0, 1.1, 1.2, 1.3, or 1.4 mg/g.

The composition for use in the treatment and/or prevention of vestibulodynia according to the present document may, based on the total weight of the composition, e.g. comprise or consist of:
- from about 3 to about 4 wt %, such as about 3 to about 3.5 wt %, such as about 3.2 wt % hydroxypropylmethylcellulose (HPMC),
- a lactate buffer in a concentration of from about 20 to about 40 mM, such as 25 mM,
- optionally a preservative, such as benzoic acid, in a concentration of from about 0.5 to about 1.5 mg/g, and
- an aqueous solvent such as water,
- said composition having a pH within the range of from about 3.5 to about 4, such as about 3.8.

The composition may consist of one or more non-ionic cellulose ether(s), one or more pH regulating agent(s), optionally one or more preservative(s) and an aqueous solvent, such as water.

It was surprisingly found that a composition as disclosed herein had a medical effect on vestibulodynia, despite the lack of an active pharmaceutical ingredient other than the non-ionic cellulose ether optionally in combination with the pH adjuster in the composition. While not wishing to be bound by any specific theory, it is believed that the non-ionic cellulose ether optionally in combination with the pH adjuster exerts the pharmacological effect observed for the composition described herein. It is a significant benefit that the composition is non-cytotoxic. Also, as the composition comprises so few ingredients, the risk for adverse reactions against it is decreased.

The composition disclosed herein may be prepared by gently mixing the one or more non-ionic cellulose ethers with water and optionally one or more pH regulating agents and/or one or more preservatives. The mixing may be performed at room temperature or at elevated temperature above the clouding temperature of the one or more non-ionic cellulose ethers.

The composition described herein may be a gel such as an aqueous gel.

Uses of the Composition

The composition of the present document may be used in the treatment and/or prevention of vestibulodynia.

The present document is thus directed to a composition as disclosed herein for use in the treatment and/or prevention of vestibulodynia. The present document is also directed to a method for treating and/or preventing vestibulodynia, wherein said method comprises administration of a (therapeutically) effective amount of a composition as described herein to a subject in need thereof. The present document is further directed to the use of a non-ionic cellulose ether as defined herein for the manufacture of a (therapeutic) composition for the treatment and/or prevention of vestibulodynia.

The composition may be administered to one or more of the following: the vulva, the vulval vestibule, the vaginal introitus, the vagina. It will be appreciated that administration to the vagina will include administration to the vaginal introitus. As used herein, administration to the vagina is understood to include administration to the vaginal introitus. Typically, from about 0.5 to about 2 ml (per area of application) of the composition is administered to one or more of these areas. Typically, from about 0.5 to about 1.5 ml of the composition is administered to the vulval vestibule and/or from about 0.5 to about 1.5 ml of the composition is administered to the vagina including the vaginal introitus. Preferably, the composition is at least administered to the vulval vestibule.

The composition is typically administered once daily, although it is possible to administer the composition two or more times a day, such as 2, 3, 4, or 5 times a day. The composition is preferably administered at least when going to bed.

The composition may be applied topically such as by topical application using the fingers. Alternatively, an applicator, such as a syringe, may be used.

The vestibulodynia described herein may have taken place for a time period equal to or above about 6 months, such as equal to or above about 1, about 2, about 3, about 4 or about 5 years. For instance, the vestibulodynia may have taken place for a time period from about 6 months to about 10 years, such as from about 1 year to about 10 years, such as from about 1 year to about 5 years. This represents a long time suffering for the women being afflicted by the vestibulodynia and the pain associated therewith. Unexpectedly, it has been found that vestibulodynia can be successfully treated with the composition described herein thereby reducing or even removing the symptoms such as pain associated with the vestibulodyina.

The present document is also directed to the use of hydroxypropylmethylcellulose for the treatment and/or prevention of vestibulodynia.

ITEMS

Item 1

A composition comprising:
at least one non-ionic cellulose ether,
one or more pH regulating agent(s), and
an aqueous solvent,
said composition having a pH from about 3 to about 5, a viscosity from about 35000 to about 100 000 mPas and being free from any additional active pharmaceutical agent for use in the treatment and/or prevention of vestibulodynia.

Item 2

The composition for use according to item 1, wherein said composition has a viscosity of from about 35000 to about 100 000, from about 38 000 to about 100 000, from about 40 000 to about 100 000, from about 45 000 to about 100 000, from about 47 000 to about 100 000, from about 50 000 to about 100 000, from about 52 000 to about 100 000 or from about 55 000 to about 100 000 mPas.

Item 3

The composition for use according to item 1 or 2, wherein the osmolality is from about 10 to about 300 mOsmol/kg, such as from about 10 to about 200 mOsmol/kg, from about 20 to about 100 mOsmol/kg, from about 30 to about 50 mOsmol/kg, or from about 40 to about 50 mOsmol/kg.

Item 4

The composition for use according to any one of the preceding items, wherein said composition has a pH within the range of from about 3 to about 4.5, such as from about 3.2 to about 4.0, from about 3.5 to about 4.0, or from about 3.7 to about 3.9, such as about 3.8.

Item 5

The composition for use according to any one of the preceding items, wherein the pH regulating agent in said composition comprises a buffer, such as a lactate and/or citrate buffer.

Item 6

The composition for use according to any one of the preceding items, said composition further comprising a preservative, such as benzoic acid.

Item 7

The composition for use according to any one of the preceding items, wherein said at least one non-ionic cellulose ether is selected from the group consisting of methylcellulose (MC), hydroxypropylcellulose (HPC), hydroxypropylmethylcellulose (HPMC), hydroxyethylethylcellulose (HEEC), hydroxyethylmethylcellulose (HEMC) and any combination thereof.

Item 8

The composition for use according to any of the preceding items, wherein said at least one non-ionic cellulose ether is hydroxypropylmethylcellulose (HPMC).

Item 9

The composition for use according to any one of the preceding items, wherein said composition comprises from about 1 wt % to about 5 wt %, about 2 wt % to about 4 wt %, such as from about 3 wt % to about 4 wt %, such as about 3 wt % to about 3.5 wt %, such as about 3.2 wt % of said non-ionic cellulose ether based on the total weight of the composition.

Item 10

The composition for use according to any one of the preceding items, wherein said composition comprises or consists of, based on the total weight of the composition:
- from about 3 wt % to about 4 wt %, such as about 3 wt % to about 3.5 wt %, such as about 3.2 wt % of hydroxypropylmethylcellulose (HPMC),
- a lactate buffer in a concentration of from about 20 to about 40 mM, and optionally a preservative, such as benzoic acid, in a concentration of from about 0.5 to about 1.5 mg/g, and
- an aqueous solvent,
- said composition having a pH within the range of from about 3.5 to about 4, such as about 3.8.

Item 11

The composition for use according to any one of the preceding items, wherein the aqueous solvent is water.

Item 12

The composition for use according to any one of the preceding items, wherein the vestibulodynia is generalized vestibulodynia or localized vestibulodynia.

Item 13

The composition for use according to any one of the preceding items, wherein the vestibulodynia occurs in the absence of touching or application of pressure to the vulva and/or vaginal introitus.

Item 14

The composition for use according to any one of items 1-12, wherein the vestibulodynia occurs in the presence of touching or application of pressure to the vulva and/or vaginal introitus.

Item 15

The composition for use according to any one of the preceding items, wherein the vestibulodynia is not associated with sexual intercourse.

Item 16

The composition for use according to any one of items 1-14, wherein the vestibulodynia is associated with sexual intercourse.

Item 17

The composition for use according to any one of the preceding items, wherein said composition is administered at least once daily, such as one to five times a day.

Item 18

The composition for use according to any one of the preceding items, wherein said composition is administered to the vulva and/or the vaginal introitus.

Item 19

The composition for use according to any one of the preceding items, wherein said composition is administered in an amount of from about 0.5 to about 1.5 ml to the vulva and/or the vaginal introitus.

Item 20

A method for treating and/or preventing vestibulodynia, said method comprising administering a therapeutically effective amount of a composition as defined in any one of items 1-11 to a subject, such as a woman, in need thereof.

Item 21

The method according to item 20, wherein the vestibulodynia is generalized vestibulodynia or localized vestibulodynia.

Item 22

The method according to item 20 or 21, wherein the vestibulodynia occurs in the absence of touching or application of pressure to the vulva and/or vaginal introitus.

Item 23

The method according to item 20 or 21, wherein the vestibulodynia occurs in the presence of touching or application of pressure to the vulva and/or vaginal introitus.

Item 24

The method according to any one of items 20-23, wherein the vestibulodynia is not associated with sexual intercourse.

Item 25

The method according to any one of items 20-23, wherein the vestibulodynia is associated with sexual intercourse.

Item 26

The method according to any one of items 20-25, wherein said composition is administered at least once daily, such as one to five times a day.

Item 27

The method according to any one of items 20-26, wherein said composition is administered to the vulva and/or the vaginal introitus.

Item 28

The method according to any one of items 20-27, wherein said composition is administered in an amount of from about 0.5 to about 1.5 ml to the vulva and/or the vaginal introitus.

Item 29

Use of a non-ionic cellulose ether for the manufacture of a composition as defined in any one of items 1-11 for the treatment and/or prevention of vestibulodynia.

Item 30

The use according to item 29, wherein the vestibulodynia is generalized vestibulodynia or localized vestibulodynia.

Item 31

The use according to item 29 or 30, wherein the vestibulodynia occurs in the absence of touching or application of pressure to the vulva and/or vaginal introitus.

Item 32

The use according to any one of items 29 or 30, wherein the vestibulodynia occurs in the presence of touching or application of pressure to the vulva and/or vaginal introitus.

Item 33

The use according to any one of items 29-32, wherein the vestibulodynia is not associated with sexual intercourse.

Item 34

The use according to any one of items 29-32, wherein the vestibulodynia is associated with sexual intercourse.

Item 35

The use according to any one of items 29-34, wherein said composition is administered at least once daily, such as one to five times a day.

Item 36

The use according to any one of items 29-35, wherein said composition is administered to the vulva and/or the vaginal introitus.

Item 37

The use according to any one of items 29-36, wherein said composition is administered in an amount of from about 0.5 to about 1.5 ml to the vulva and/or the vaginal introitus.

The invention will be further described in the following examples, which do not limit the scope of the invention described in the claims.

EXPERIMENTAL SECTION

General

The equipment used for mixing was a Unimix SRT 15. The hypromellose used was Benecel K15M Pharm.

Example 1: Pharmaceutical Composition Manufacturing

The components of Table 1 were mixed as follows. Purified water (1 371 g) was added to a container followed by lactic acid (33 g). Mixing was performed until a homogeneous solution, as indicated by visual inspection, was obtained. The pH of the homogenous solution was measured and found to be 2.72. The pH was adjusted to 3.72 by addition of a 5 M aqueous solution of NaOH. Thereafter, purified water was added (719.3 g) followed by benzoic acid (15 g) at a mixing speed of 4.5 rpm. Homogenization was activated for 125 s at a mixing speed of 4.5 rpm. Mixing was continued for 90 minutes. Then, visual inspection revealed that all benzoic acid was dissolved. The solution was allowed to assume room temperature, and then hypromellose (450 g) was added to the solution. The resulting solution was mixed at about 12° C. at a mixing speed of about 2.5 rpm for 121 minutes. During this time, the homogenizer was activated for about 1 minute. Thereafter, mixing was continued at a mixing speed of about 2.5 rpm at room temperature for 18 hours. The resulting gel was homogenous as shown by visual inspection. No lumps or air bubbles were present.

TABLE 1

| Component | Amount per batch (g) |
|---|---|
| Benzoic acid | 15 |
| Lactic acid | 33 |
| Sodium hydroxide 5M | q.s.* |

TABLE 1-continued

| Component | Amount per batch (g) |
|---|---|
| Hypromellose | 450 |
| Purified water | q.s.** |

*To a pH of 3.75 (q.s. stands for quantum satis)
**To a final weight of 15000 g

Visual inspection showed that the gel was substantially clear. The viscosity was measured at 20° C. according to European Pharmacopoeia 7.0, 2.2.10 at 1-12 rpm as well as the pH was measured providing values shown in Table 2. The pH was 3.6.

TABLE 2

| Mixing speed in rpm | Viscosity value in mPas |
|---|---|
| 1 | 62500 mPas |
| 3 | 50167 mPas |
| 5 | 43800 mPas |
| 10 | 35100 mPas |
| 12 | 32833 mPas |

Example 2: Pharmaceutical Composition Manufacturing

The components of Table 3 were mixed as follows. Purified water was added to a Krieger manufacturing vessel and heated to 70° C. followed by the addition of lactic acid. Homogenizing was performed at 1500 rpm for 2 min until a homogeneous solution, as indicated by visual inspection, was obtained. 2 M aqueous solution of NaOH was then added with a target pH of 3.85 and further homogenized at 1500 rpm for 2 min. This was followed by the addition of benzoic acid at a homogenizing speed of 1500 rpm for 5 min. Visual inspection revealed that all benzoic acid was dissolved. Then hypromellose was added to the solution which temperature was maintained at 70° C. The resulting mixture was homogenized at a mixing speed of 2000 rpm until the temperature had reached 60° C.

Mixing was continued during cooling to 15° C. The resulting gel was homogenous as shown by visual inspection. No lumps or air bubbles were present.

TABLE 3

| Ingredients | Amount (1000 kg) | Function |
|---|---|---|
| Purified water | q.s.**** | Solvent |
| (S)-lactic acid | 2.2 kg | Buffering agent |
| Sodium hydroxide 2M solution* | 6.0 kg** | Buffering agent |
| Benzoic acid | 1.0 kg | Preservative |
| Hydroxypropylmethylcellulose | 32 kg*** | Gelling agent |

Example 3: Clinical Effect of the Pharmaceutical Composition of Example 2 in Women With Vestibulodynia 17 women between 18 and 45 years of age with diagnosed vestibulodynia took part in the study. The women had experienced the problems for at least a year.

The women were instructed to apply the gel on the outer parts of the vagina, i.e. the vulva, with the fingers and optionally also intravaginally (4-5 cm into the vagina) including the vaginal introitus with an applicator. The treatment period was one month or more. The composition was applied once a day and left at the site of application.

Figure 2:
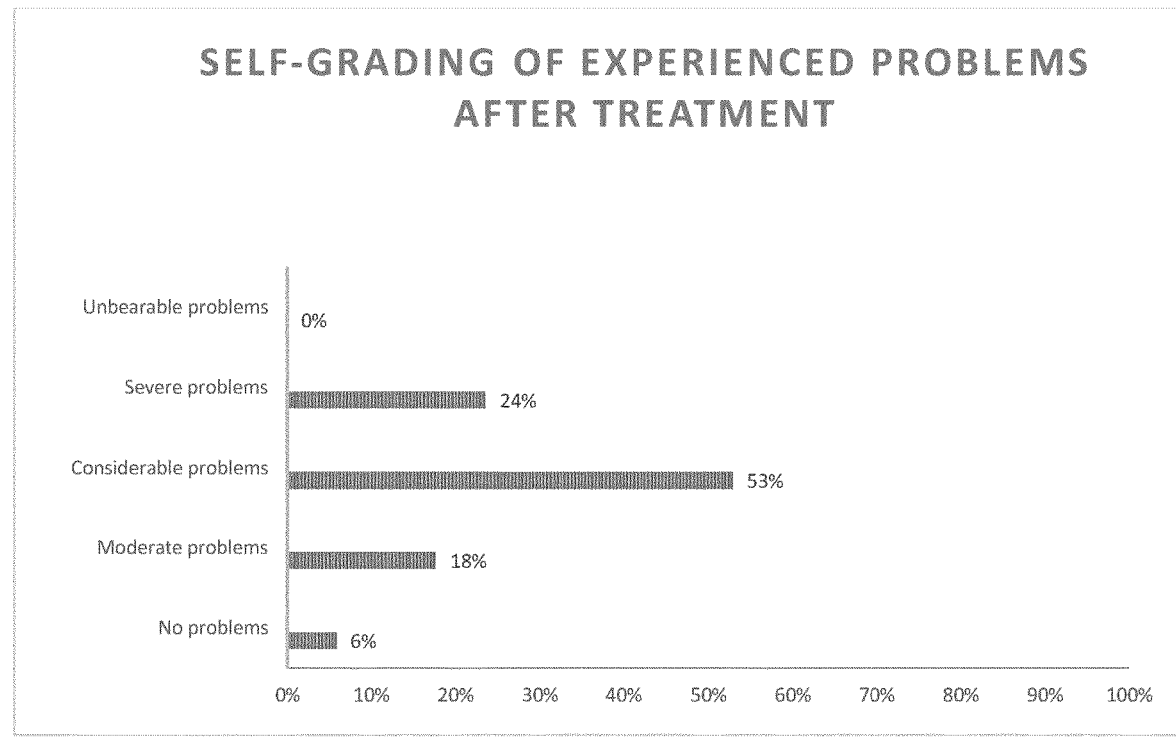
FIG. 2 show a grading of the experienced problems with vestibulodynia after treatment with the composition of Example 2.
Figure 3:
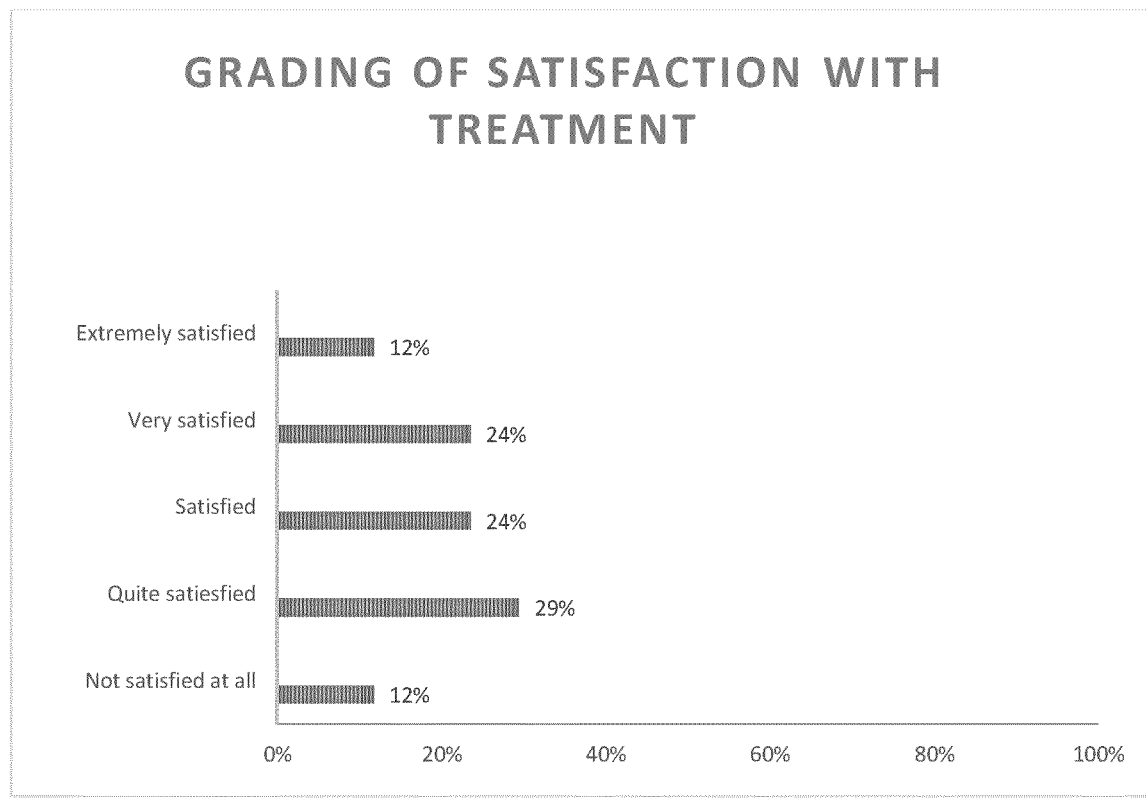
FIG. 3 shows a grading of the degree of satisfaction with the treatment with the composition of Example 2.
Figure 4:
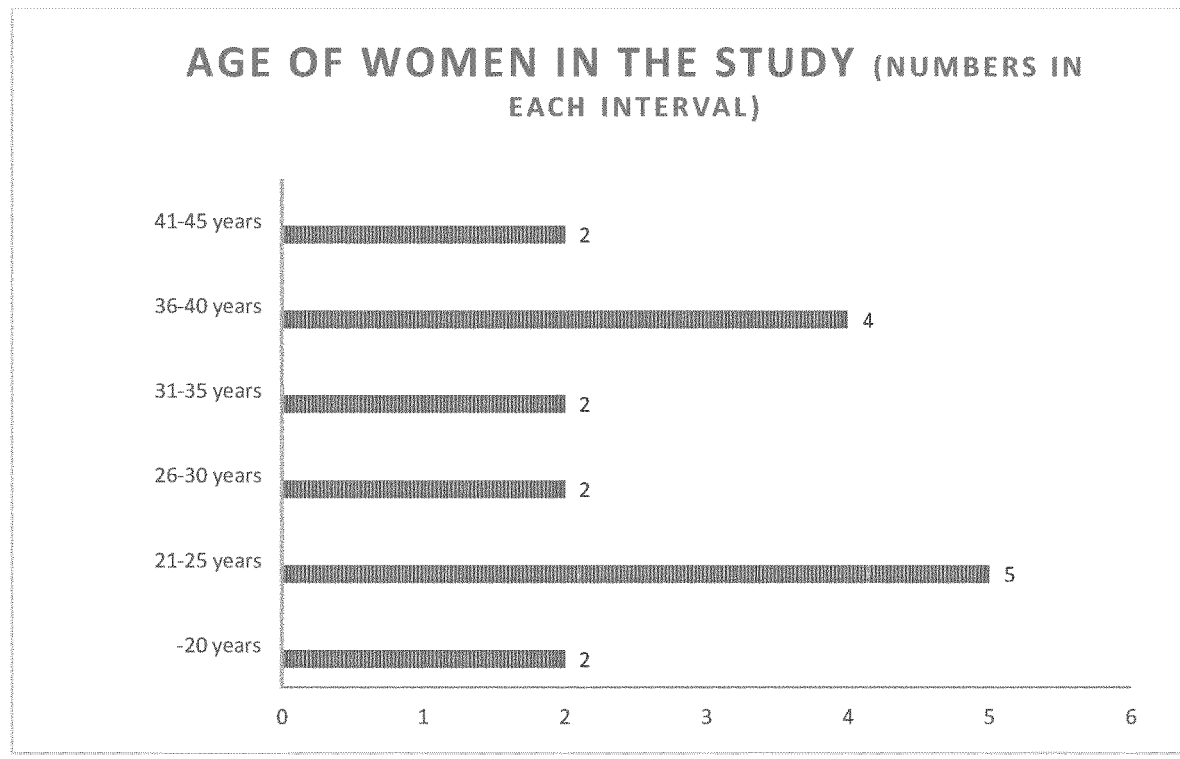
FIG. 4 shows a diagram of the age of the women in the study.

FIG. 1 shows the experienced problems before treatment with the composition of Example 2 and FIG. 2 the problems experienced after treatment. FIG. 3 indicates the level of satisfaction with the treatment. FIG. 4 show the age distribution among the women in the study.

As can be seen when comparing FIGS. 1 and 2, there was a clear improvement of the symptoms of vestibulodynia in the group of women, independently on how severe the problems were before treatment. In particular it is worth noting that no woman experienced almost unbearable problems after treatment (2 before treatment) and only 4 women experienced severe problems after treatment as opposed to 10 before the treatment was initiated. One woman even experienced no symptoms at all after the treatment.

These data thus confirm that the composition of the present document is efficient in the treatment and/or prevention of vestibulodynia.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

The invention claimed is:

1. A method for treating and/or preventing vestibulodynia, said method comprising administering a therapeutically effective amount of a composition comprising:
    at least one non-ionic cellulose ether, said at least one non-ionic cellulose ether being hydroxypropylmethylcellulose (HPMC),
    one or more pH regulating agent(s) comprising a lactate and/or a citrate buffer, and water,
    said composition having a pH from 3 to 5,
    a viscosity from 35000 to 100 000 mPas, said viscosity being measured at 20° C. according to European Pharmacopoeia 7.0, 2.210, and
    being free from any additional active pharmaceutical agent
    wherein said composition comprises from 1 wt % to 5 wt % of said non-ionic cellulose ether based on the total weight of the composition,
    to a subject in need thereof.
2. The method according to claim 1, wherein the vestibulodynia is generalized or localized vestibulodynia, and/or has taken place for a time period equal to or above 6 months.
3. The method according to claim 1, wherein the vestibulodynia occurs in the absence of touching or application of pressure to the vulva.
4. The method according to claim 1, wherein the vestibulodynia occurs in the presence of touching or application of pressure to the vulva.
5. The method according to claim 1, wherein the vestibulodynia is not associated with sexual intercourse.
6. The method according to claim 1, wherein the vestibulodynia is associated with sexual intercourse.
7. The method according to claim 1, wherein said composition is administered at least once daily.

8. The method according to claim 1, wherein said composition is administered to the vulva.

9. The method according to claim 1, wherein said composition is administered in an amount of from 0.5 to 1.5 ml to the vulva.

10. The method according to claim 1, wherein the composition has a viscosity of from 38 000 to 100 000 mPas.

11. The method according to claim 1, wherein the composition has a osmolality from 10 to 300 mOsmol/kg.

12. The method according to claim 1, wherein the composition has a osmolality from 40 to 100 mOsmol/kg.

13. The method according to claim 1, wherein said composition has a pH within the range of from 3 to 4.5.

14. The method according to claim 1, wherein the pH regulating agent in said composition comprises a lactate buffer.

15. The method according to claim 1, wherein said composition comprises a preservative.

16. The method according to claim 1, wherein said composition comprises from 2 wt % to 4 wt % of said non-ionic cellulose ether based on the total weight of the composition.

17. The method according to claim 1, wherein said composition comprises based on the total weight of the composition:
   from 3 wt % to 4 wt % hydroxypropylmethylcellulose (HPMC),
   a lactate buffer in a concentration of from about 20 to about 40 mM, and water,
   wherein said composition has a pH within the range of from 3.5 to 4.

18. The method according to claim 1, wherein the composition further comprises a preservative in a concentration of from 0.5 to 1.5 mg/g.

19. The method according to claim 1, wherein the subject is a woman.

20. The method according to claim 1, wherein the composition further comprises a preservative.

* * * * *